United States Patent [19]
Hodgkin et al.

[11] Patent Number: 5,708,127
[45] Date of Patent: Jan. 13, 1998

[54] POLYMERIZABLE MONOMERIC REACTANTS (PMR) TYPE RESINS

[75] Inventors: Jonathan Howard Hodgkin; Robert Eibl, both of Victoria, Australia

[73] Assignee: Commonwealth Scientific and Industrial Research Organisation, Campbell, Australia

[21] Appl. No.: 446,725

[22] PCT Filed: Dec. 7, 1993

[86] PCT No.: PCT/AU93/00623

§ 371 Date: Jul. 21, 1995

§ 102(e) Date: Jul. 21, 1995

[87] PCT Pub. No.: WO94/13670

PCT Pub. Date: Jun. 23, 1994

[30] Foreign Application Priority Data

Dec. 7, 1992 [AU] Australia ............... PL 6234/92

[51] Int. Cl.⁶ ................... C08G 73/10; C08G 69/26
[52] U.S. Cl. ................... 528/353; 528/125; 528/126; 528/128; 528/170; 528/172; 528/173; 528/179; 528/183; 528/186; 528/188; 528/220; 528/229; 528/310; 528/322; 528/351; 525/935; 524/600; 524/607; 428/395; 428/411.1; 428/473.5
[58] Field of Search ............... 528/128, 126, 528/125, 353, 220, 229, 172, 170, 173, 310, 179, 322, 183, 186, 188, 351; 428/395, 473.5, 411.1; 526/935; 524/600, 607

[56] References Cited

U.S. PATENT DOCUMENTS

| | | | |
|---|---|---|---|
| 3,998,786 | 12/1976 | D'Alelio . | |
| 5,041,526 | 8/1991 | Riel et al. | 528/128 |
| 5,041,527 | 8/1991 | Riel et al. | 528/353 |
| 5,041,528 | 8/1991 | Riel et al. | 528/353 |

FOREIGN PATENT DOCUMENTS

| | | |
|---|---|---|
| B-28625/57 | 12/1957 | Australia . |
| B-50572/72 | 7/1974 | Australia . |
| A-86280/91 | 4/1992 | Australia . |

*Primary Examiner*—James J. Seidleck
*Assistant Examiner*—P. Hampton-Hightower
*Attorney, Agent, or Firm*—Bacon & Thomas

[57] ABSTRACT

The invention relates to a PMR type resin which comprises a mixture of:

(a) nadic acid of Formula (Ia) or a derivative thereof

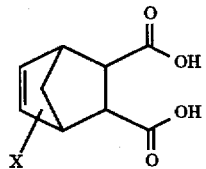

Formula (Ia)

(b) a diaminobisimide of Formula (Ib)

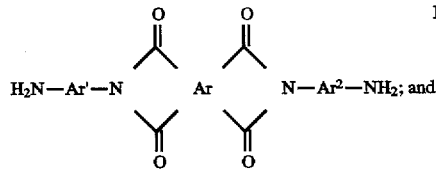

Formula (Ib)

(c) an aromatic tetracarboxylic acid of Formula (Ic) or a derivative thereof

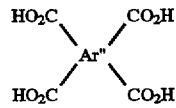

Formula (Ic)

the components (a), (b) and (c) being present in the approximate molar proportions of 2:n:n−1 respectively.

22 Claims, No Drawings

POLYMERIZABLE MONOMERIC REACTANTS (PMR) TYPE RESINS

The invention is concerned with polymerizable monomeric reactants (PMR) type resins containing bisnadimide and high temperature resistant matrix polymers for composites made therefrom.

In recent years the most practical of the high temperature thermostable polyimide matrix resins developed for the aerospace industry has been the polymerizable monomeric reactants (PMR) type, produced by workers in NASA, USA. These resins are monomeric mixtures of aromatic diamines with nadic anhydride and aromatic dianhydride based esters. These mixtures were reported to react at intermediate temperature to give nadimide capped oligomers of Formula (I) as shown below.

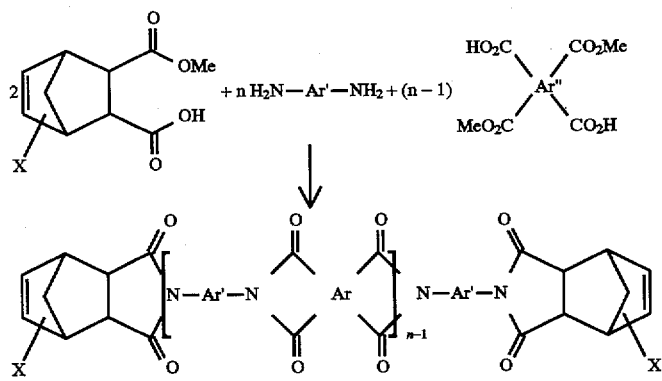

Formula (I)

At higher cure temperatures, these oligomers melt and crosslink to form a continuous stable matrix in advanced composite structures. Recent work (J. N. Hay, J. D. Boyle, P. G. James, J. R. Walton, and D. Wilson, "Polymerisation Mechanisms in PMR 15 Polyimide.", in *Polyimides: Materials, Chemistry and Characterization*, C. Feger, M. M. Khojasteh, and J. E. McGrath Eds., Elsevier, Amsterdam, 1989, pages 305 to 320) has shown that the oligomers formed have much more complex structures with unreacted ester and acid groups as well as uncyclized structures. This complexity and partial reaction means that consistent resin properties are not possible and also lead to brittleness, microcracking and voids in the final composites. The aromatic diamine monomers present in the resins often have toxicity and stability problems, for example, diaminodiphenylmethane—the most commonly used aromatic diamine in industry.

An alternative approach to improve composite toughness, etc., has been to use higher molecular weight or fluorinated monomers in the initial resin mixtures and hence improve molecular mobility and processability. The difficult challenge however is to prepare relatively homogeneous materials without increasing material costs greatly.

International Patent Publication No. WO 92/06078 by the present applicant, which is incorporated herein by reference, describes a process for the low cost production of novel, high molecular weight monomeric diaminobisimides (hereinafter referred to as "DABIs") of well defined structure and substantially free of oligomeric, amidic and uncyclized impurities. These aromatic diamines have also been found to be non-toxic and stable. International Patent Publication No. WO 92/06078 also discloses the use of DABIs as hardeners for epoxy resins.

In European Patent Publication No. 0 479 722 A2, Kramer et al disclose oligomeric polyimides of Formula (I) as defined above wherein Ar is $C_6H_2$ and $5<n<150$. These polyimides are stated to be soluble and useful as tougheners in crosslinked resin systems.

We have now found that DABIs produced by the process disclosed in International Patent Publication No. WO 92/06078 can be used to make PMR type resins which crosslink on heating to give thermally stable polyimides having much better properties than the standard PMR matrix resins.

According to one aspect of the present invention there is provided a PMR type resin which comprises a mixture of:

(a) nadic acid of Formula (Ia) or a derivative thereof

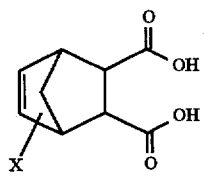

Formula (Ia)

(b) a diaminobisimide of Formula (Ib)

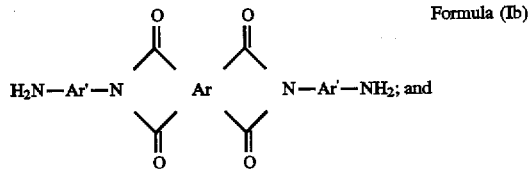

Formula (Ib)

(c) an aromatic tetracarboxylic acid of Formula (Ic) or a derivative thereof

Formula (Ic)

the components (a), (b) and (c) being present in the approximate molar proportions of 2:n:n−1 respectively; and wherein n is chosen to provide a polyimide polymer of the desired size;

Ar and Ar" may be the same or different and each represents an optionally substituted aryl, optionally substituted bridged or bonded di- or poly-aryl or optionally substituted heteroaryl group;

Ar' is an optionally substituted aryl or heteroaryl group which provides for good conjugation between the nitrogen containing groups; and X is an alkyl group or hydrogen.

Preferably 5>n>2.

As used herein the term "good conjugation" means that during formation of the diaminobisimide precursor from a diamine of Formula (III) shown below, substitution of an electron-withdrawing group on one of the nitrogen atoms suppresses the reactivity of the other nitrogen atom during the reaction.

Formula (III)

Preferably the aromatic diamine of the Formula (III) is sterically hindered, such as in compounds of Formulae (V) and (VI)

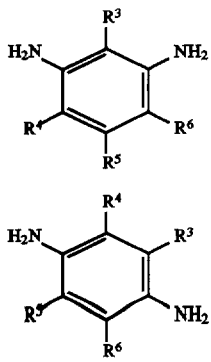

Formula (V)

Formula (VI)

wherein $R^3$, $R^4$, $R^5$ and $R^6$ are the same or different and each may be selected from alkyl, aryl, heteroaryl, nitro and halogen groups.

Ar, Ar' or Ar" may be substituted with one or more alkyl, alkoxy, arylthio, aryl, heteroaryl, aryloxy, carboxy, alkylthio, alkylamino, dialkylamino, amino, nitro, cyano or halo groups.

"Aryl" means an aromatic carboxylic group, such as phenyl, naphthyl, and the like.

"Bridged or bonded di- or poly-aryl" means a group consisting of two or more aromatic carboxylic ring system, such as phenyl, naphthyl or the like joined by a bond, such as in biphenyl, or a bridging group, such as in sulphonyl-diphenyl.

"Bridging group" includes for example $SO_2$, CO, $CH_2$ and O such as in compounds of the Formula (VIIa)

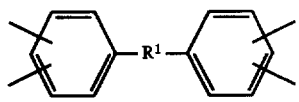

Formula (VIIa)

wherein $R^2$ is a divalent group such as —$SO_2$—, —CO—, —$CH_2$— and —O—.

Generally the group Ar' may be selected from the groups listed above for Ar. However, because of the constraints imposed by the requirement of "good conjugation" (as defined above) some bridged di- or poly-aryl groups may not be suitable. Thus for Ar', the bridging group (if present) must provide good conjugation between the amino groups of the diamine moiety (III). For example in groups of the Formula (VIIb)

Formula (VIIb)

wherein $R^1$ is $CH_2$ or where the diamine is 3,3'-sulphonyldianiline, there is insufficient conjugation and oligomeric diaminoimides are present in the precursor diaminobisimides. In contrast, benzidine and 4,4'-sulphonyldianilines have sufficient conjugation and give the desired predominantly monomeric diaminobisimide compound and hence a substantially monomeric bisnadimide.

"Heteroaryl" means aromatic monocyclic or polycyclic groups containing at least one heteroatom such as nitrogen, oxygen or sulfur. Examples of suitable "heteroaryl" groups are: 3- to 8- membered, more preferably 5- or 6-membered heteromonocyclic groups containing 1 to 4-nitrogen atom (s), for example, pyrrolyl, imidazolyl, pyrazolyl, pyridyl, pyrimidyl, pyrazinyl, pyridazinyl, triazinyl; condensed heterocyclic groups containing 1 to 5 nitrogen atom(s), for example, indoyl, isoindolyl, indolizinyl, benzimidazolyl, quinolyl, isoquinolyl, indazolyl, benzotriazolyl, etc.; 3 to 8-membered heteromonocyclic groups containing 1 to 2 sulfur atom(s) and 1 to 3 nitrogen atom(s), for example, thiazolyl, isothiazolyl, thiadiazolyl, etc.; 3- to 8- membered heteromonocyclic groups containing 1 to 2 sulfur atom(s), for example thienyl, etc.; condensed heterocyclic groups containing 1 to 2 sulfur atom(s) and 1 to 3 nitrogen atom(s), for example, benzothiazolyl; benzothiadiazolyl, etc.; 3- to 8-membered heteromonocyclic groups containing an oxygen atom, for example, furyl, etc.; condensed heterocyclic groups containing 1 to 2 sulfur atom(s), for example, benzothienyl, etc.; and condensed heterocyclic groups containing 1 or 2 oxygen atom(s), for example, benzofuranyl, etc.

The alkyl group maybe straight chain or branched and contain 1 to 20 carbon atoms. Suitable alkyl groups are methyl, ethyl, propyl, iso-propyl, n-butyl, iso-butyl, tert-butyl, n-pentyl, iso-pentyl, neo-pentyl, n-octyl, iso-octyl, decyl, cetyl, stearyl, and the like.

"Alkoxy" and "alkylthio" mean groups in which the alkyl moiety is a branched or unbranched saturated hydrocarbon group containing from one to eight carbon atoms, such as methyl, ethyl, propyl, iso-propyl, n-butyl, iso-butyl, tert-butyl and the like.

"Alkanoyl" may be formyl, acetyl, propionyl, butyryl, valeryl, iso-valeryl, pivaloyl, hexanoyl, and the like.

Preferably, the diaminobismide of the formula (Ib) is produced by the method disclosed in International Patent Publication No. WO 92/06078 as such a compound is substantially free of oligomeric, amidic and uncyclized impurities. However, it will be appreciated that the diaminobisimide of the formula (Ib) used in the method of the invention may be produced by any suitable known process.

On curing at an elevated temperature, the resins of the invention may be convened by the normal PMR curing mechanisms via an oligomeric intermediate into crosslinked polyimide polymers having improved properties. These polyimide polymers are useful for a variety of applications including adhesives, bars, films, electronic encapsulation moulded components and composites.

According to another aspect of the present invention there is provided art oligomeric intermediate of Formula (Id)

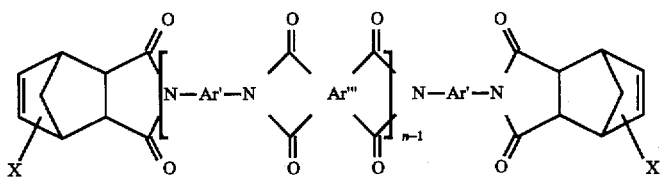

Formula (Id)

wherein

Ar' and X are as defined above;

Ar'" is Ar or Ar" as defined above; and

5<n>2.

According to a further aspect of the present invention there is provided a polyimide polymer formed from a PMR type resin or an oligomeric intermediate as defined above.

There is also provided a method for the preparation of a polyimide polymer which comprises heating a PMR type resin or an oligomeric intermediate as defined above.

By utilising the present invention, the PMR type resin containing a toxic reactive diamine of conventional practice is replaced by one containing a safe, stable diamine which can be readily handled during composite fabrication. Furthermore, on a weight of resin basis, much lower quantities of volatile cyclization products are evolved during the during step as at least half the groups are already cyclized.

Some of the PMR type resins provided by the invention can be made by variations on methods already in the prior art by using the DABIs described in International Patent Publication No. WO 92106078 in place of the toxic diamine methylene dianiline. However, for the more insoluble DABIs higher temperatures and more prolonged reaction with the mixed nadic and tetracarboxylic dianhydride type esters are required to ensure complete reaction.

While the prior art describes very few co-reactants for curing PMR type resins, it has been found that trans-stilbene is a particularly good curing additive for the PMR-type resin of the invention. Another additive particularly useful in the production of void free resin bars from the compositions of this invention is the addition of a small percentage of hydroquinone or other additive to prevent "skinning" and hence entrapment of residual volatiles during the early stages of cure.

The PMR type resins of the present invention are particularly useful in the manufacture of fibre reinforced composite materials. For example, the PMR type resins of the invention may be applied to reinforcing cloth such as uni-directional or woven carbon fibre either from solution (preferably a lower aliphatic ketone or halogenated hydrocarbon solvent) or from a hot melt. Application may be performed manually or by machine and includes techniques involving transfer from a precoated transfer medium.

Thus, the present invention also provides an impregnated fibre reinforced material (commonly known as "prepreg") wherein the fibre reinforcements are coated with a PMR type resin or an oligiomeric intermediate as defined above.

The impregnated fibre reinforced materials are suitable for use in the production of advanced composite materials. The impregnated fibre materials can be laid down by any suitable known method for making composite materials, such as, for example, vacuum bagging on a caul plate or an appropriate tool.

Accordingly, the present invention further provides an advanced composite material which comprises an assembly of reinforcing fibres in a matrix of an oligiomeric intermediate or a polyimide polymer as defined above.

Alternatively, the composition of the invention can be used in an appropriate formulation for resin transfer moulding or for the manufacture of sheet moulded material. Another envisaged application is in pultrusion.

The invention is illustrated by the following Examples. These Examples are not to be construed as limiting the invention in any way.

The systematic names used in the Examples are based on the Chemical Abstracts names of related compounds.

EXAMPLE 1

PMR type resin, CBR-151, Formulae (Ia), (Ib) and (Ic) wherein X is H, Ar and Ar" are $C_6H_3COC_6H_3$ and Ar' is 1,3 distributed methyldiethylphenyl (a) Resin Manufacture A solution of nadic anhydride (32.4 g, 0.20 mole) and 3,3',4,4' benzophenone tetracarboxylic dianhydride (32.2 g, 0.10 mole) in 250 mls of methanol was heated to 50° C. for 0.5 hrs to form the methyl esters. 5,5-carbonylbis-{2-[3-amino(methyldiethyl)phenyl]}-1H-isoindole-1,3(2H)-dione prepared by the method as described in International Patent Publication No. WO 92/06078 (28.6 g, 0.10 mole) was added slowly with stirring and heating to reflux for 1 hour. The solution was then heated under vacuum on a "rotovac" slowly over 4 hours to 200° C. to give a light brown molten mass of the resin which remained soluble in trichloroethylene and acetone.

Infrared spectra showed peaks at 1777 and 1717 $cm^{-1}$ (imide), 1674 $cm^{-1}$ (carbonyl) 1182, 1105 and 723 $cm^{-1}$.

(b) Prepreg Manufacture and Curing

A prepreg was prepared on 0.5 $m^2$ carbon-fibre cloth (SPS) plain weave with 40–45% resin content. This was laid up into a five layer plaque and cured in a platen press with the following cure profile:

1 hr to 220° C., held at temperature for 2 hrs, 1 hr to 260° C., held for 3 hrs, 280° C. for 1 hr. This was followed by a free standing post cure at 300° C. under nitrogen for 3 hrs.

Up to the 260° C. stage only light pressure (about 20 psi) was applied but above this the highest available pressure ≈180 psi was used.

Dynamic Mechanical Thermal Analysis (DMTA) of this sample using a Polymer Laboratories Analyser demonstrated that the cured composite had a bending modulus ($E^1$) of over 3500 MPa up to 250° C., and a $T_g$ of 315° C.

EXAMPLE 2

A PMR type resin (CBR-151) was prepared using the process described in Example 1 except ethanol was used as a solvent. The product resin was coated onto carbon cloth in an acetone/dimethylformamide solvent (7.5/2.5% ) as a mixture with 15% Ultem anhydride (fluxing agent from General Electric Co.) to form a prepreg. A five layer composite plaque was produced as in Example 1(b) from this prepreg.

DMTA measurements showed a bending modulus ($E^1$) exceeding 3500 MPa at temperatures up to 250° C., and a $T_g$ of 305° C.

EXAMPLE 3

PMR type resin CBR-450, Formulae (Ia), (Ib) and (Ic), wherein X is H, Ar $C_6H_3CH_2C_6H_3$, Ar" $C_6H_3C(CF_3)_2C_6H_3$ and Ar' is 1,3 disubstituted methyldiphenyl (a) Resin Manufacture A solution of nadic anhydride (2.26 g, 0.014 mole) and hexafluoroisopropylbisphthalic anhydride, 6FDA (2.56 g, 0.007 mole) in 90 mls of methanol was heated to reflux for 3 hrs and then heated a further 3 hrs with methylenebis-{2-[3-amino(methyldiethyl)phenyl]}-1H-isoindole-1,3(2H)-dione prepared by the method described in International Patent Publication No. WO 92/06078 (10.0 g, 0.014 mole). The methanol was removed on a rotary evaporator and the resin heated slowly to 190° C. under vacuum for 3 hrs to give a light brown solid soluble in trichlorethylene and acetone.

Infrared spectra showed peaks at 1777 and 1715 cm$^{-1}$ (imide), 1253, 1102, 743 and 719 cm$^{-1}$.

(b) Prepreg Manufacture and Curing

A prepreg was prepared on 0.5 m² carbon-fibre cloth (SPS) plain weave with 43% resin content. This was laid up into a five layer plaque and cured in a platen press with the following cure profile:

1 hr to 200° C., held for 2 hrs, ½ hr to 250° C., held for 6 hrs, and pressure ≈180 psi applied to 315° C. in ½, held for 2 hrs and cool over 2 hrs.

DMTA measurements showed a $T_g$ of 306° C., and a bending modulus ($E^1$) exceeding 3200 MPa at temperatures up to 270° C.

EXAMPLE 4

PMR type resin CBR-160, Formulae (Ia), (Ib) and (Ic), wherein X is H, Ar is

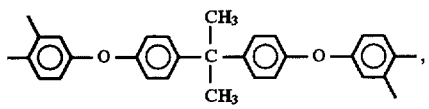

Ar' is 1,4-diphenylene and Ar" is $C_6H_3COC_6H_3$.

(a) Resin Manufacture

The resin was made using the procedure of Example 2. The product was a light brown powder insoluble in acetone and chlorinated solvents. Infrared spectra showed peaks at 1776 and 1718 cm$^{-1}$ (imide) and 1674 cm$^{-1}$ (carbonyl).

(b) Prepreg Manufacture and Curing

A prepreg was prepared on carbon-fibre cloth using powder prepregging techniques and cured into a strong five layer plaque as for Example 1(b). DMTA measurements showed a $T_g$ of 265° C.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

We claim:

1. A resin which comprises a mixture of:

(a) nadic acid of Formula (Ia) or a derivative thereof

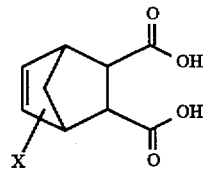

Formula (Ia)

(b) a diaminobisimide of Formula (Ib)

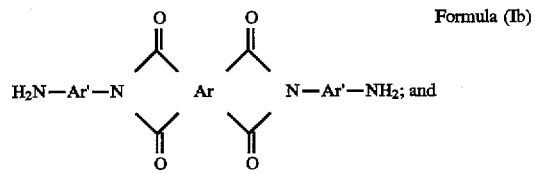

Formula (Ib)

(c) an aromatic tetracarboxylic acid of Formula (Ic) or a derivative thereof

Formula (Ic)

the components (a), (b) and (c) being present in the approximate molar proportions of 2:n:n−1; and wherein n is selected to provide a polyimide polymer of the desired size;

Ar and Ar" may be the same or different and each represent an optionally substituted aryl, optionally substituted bridged or bonded di- or poly-aryl, or optionally substituted heteroaryl group;

Ar' is an optionally substituted aryl or heteroaryl group which provides for good conjugation between the nitrogen containing groups; and X is an alkyl group or hydrogen.

2. An oligomeric intermediate of Formula (Id)

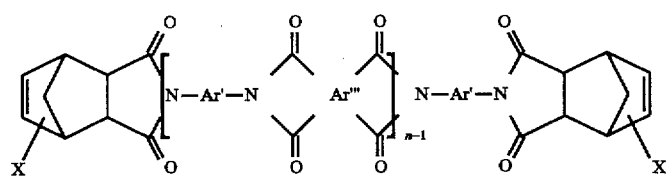

Formula (Id)

wherein

Ar' and X are as defined in claim 1;

Ar''' is Ar or Ar" as defined in claim 1; and

5>n>2.

3. A polyimide polymer formed from a resin as defined in claim 1.

4. A method for the preparation of a polyimide polymer as defined in claim 3 which comprises heating the resin.

5. A method according to claim 4, wherein the heating occurs in the presence of a curing additive.

6. A method according to claim 5, wherein the curing additive is trans-stilbene and/or hydroquinone.

7. An adhesive, bar, film or moulded component which is composed wholly or partly of a polyimide polymer as defined in claim 2.

8. An impregnated fibre reinforced material, wherein the fibre reinforcements are coated with a resin as defined in claim 1.

9. An advanced composite material which comprises an assembly of reinforcing fibres in a matrix of an oligiomeric intermediate as defined in claim 2.

10. A polyimide polymer formed from an oligomeric intermediate as defined in claim 2.

11. A method for the preparation of a polymide polymer which comprises heating an oligomeric intermediate as defined in claim 2.

12. A method according to claim 11 wherein the heating occurs in the presence of a curing additive.

13. A method according to claim 12, wherein the curing additive is trans-stilbene and/or hydroquinone.

14. An adhesive, bar, film or moulded component which is composed wholly or partly of a polyimide polymer as defined in claim 3.

15. An impregnated fibre reinforced material, wherein the fibre reinforcements are coated with an oligomeric intermediate as defined in claim 2.

16. An advanced composite material which comprises an assembly of reinforcing fibres in a matrix of a polyimide polymer as defined in claim 3.

17. A resin which is prepared by mixing a nadic acid of Formula (Ia) or a derivative thereof, with a diaminobisimide of Formula (Ib), and an aromatic tetracarboxylic acid of Formula (Ic) or a derivative thereof, in an approximate molar ratio of 2:n:n−1 each as defined in claim 1.

18. A polyimide polymer formed from a resin as claimed in claim 17.

19. A method for the preparation of a polyimide polymer as claimed in claim 18 which comprises heating the resin.

20. A method according to claim 19 wherein the heating occurs in the presence of a curing additive.

21. A method according to claim 20 wherein the curing additive is trans-stilbene and/or hydroquinone.

22. An impregnated fibre reinforced material, wherein the fibre reinforcements are coated with a resin as claimed in claim 17.

* * * * *